US00PP29140P2

(12) United States Plant Patent
Kubota

(10) Patent No.: US PP29,140 P2
(45) Date of Patent: Mar. 20, 2018

(54) ***BRASSICA* PLANT NAMED 'PURPLE VARIE'**

(50) Latin Name: *Brassica oleracea*
Varietal Denomination: Purple Varie

(71) Applicant: Takao Kubota, Isesaki (JP)

(72) Inventor: Takao Kubota, Isesaki (JP)

( * ) Notice: Subject to any disclaimer, the term of this patent is extended or adjusted under 35 U.S.C. 154(b) by 0 days.

(21) Appl. No.: 15/330,607

(22) Filed: Oct. 18, 2016

(51) Int. Cl.
*A01H 5/12* (2006.01)

(52) U.S. Cl.
USPC ..... Plt./373

(58) Field of Classification Search
USPC ..... Plt./258, 373
See application file for complete search history.

(56) References Cited

PUBLICATIONS

UPOV PLUTO: Plant Variety Database, Nov. 6, 2017, citation for 'Purple Varie'. 1 page.*

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of hybrid *Brassica*, 'Purple Varie', characterized by its vareigated foliage with green centers and pink and yellow-green margins and pink veins and its foliage that is slightly concave from mid rib with very curly margins.

2 Drawing Sheets

Botanical classification: *Brassica oleracea.*
Cultivar designation: 'Purple Varie'.

CROSS REFERENCE TO A RELATED APPLICATION

This application is related to a plant breeders' rights application filed in Japan on Mar. 24, 2015, application No. 30019. There have been no offers for sale anywhere in the world more than one year prior to the filing of this application, any sales less than one year were under the direction of the Inventor and no accessibility to one of ordinary skill in the art could have been derived from the printed plant breeder's rights documents.

BACKGROUND OF THE INVENTION

The present invention relates to a new and distinct cultivar of curly kale, botanically known as *Brassica oleracea* 'Purple Varie' and will be referred to hereafter by its cultivar name, 'Purple Varie'. The new cultivar represents a new Ornamental Kale, a plant grown as an annual for use as a container and bedding plant.

The Inventor discovered the new cultivar, 'Purple Varie', in his greenhouse in Tabei-cho, Isesaki-shi, Gunma, Japan in 2012. 'Purple Varie' was discovered as naturally occuring chimeral mutation of *Brassica oleracea* 'Scarlet' (not patented).

Asexual reproduction of the new cultivar was first accomplished by the Inventor using stem cuttings in Tabei-cho, Isesaki-shi, Gunma, Japan in 2012. Asexual reproduction by stem cuttings has determined that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Purple Varie' as a new cultivar of *Brassica.*

1. 'Purple Varie' exhibits variegated foliage with green centers and pink and yellow-green margins and pink veins.
2. 'Purple Varie' exhibits foliage that is slightly concave from mid rib with very curly margins.

'Scarlet', the parent plant of 'Purple Varie', differs from 'Purple Varie' in having foliage that is purple-red in color and foliage that is more curly. Plants of the species *Brassica oleracea* are typically green in color. 'Purple Varie' can be compared to the *Brassica oleracea* cultivar 'Panache' (not patented) and 'Kaleidoscope' (U.S. Plant Pat. No. 21,090). 'Panache' differs from 'Purple Varie' in having green foliage with variable white margins, and much less curly margins. 'Kaleidoscope' differs from 'Purple Varie' in having darker colored foliage and margins that are magenta pink to lavender in color depending on growing temperatures.

BRIEF DESCRIPTION OF THE DRAWING

The accompanying colored photographs of 'Purple Varie' illustrate the overall appearance and distinct characteristics of the new curly kale. The photographs were taken of plants 6-months in age as grown in 9-cm containers in a greenhouse in Tabei-cho, Isesaki-shi, Gunma, Japan (with a single pinch at 4 months).

The photograph in FIG. 1 provides a side view of two plants of 'Purple Varie'.

Figure 1:
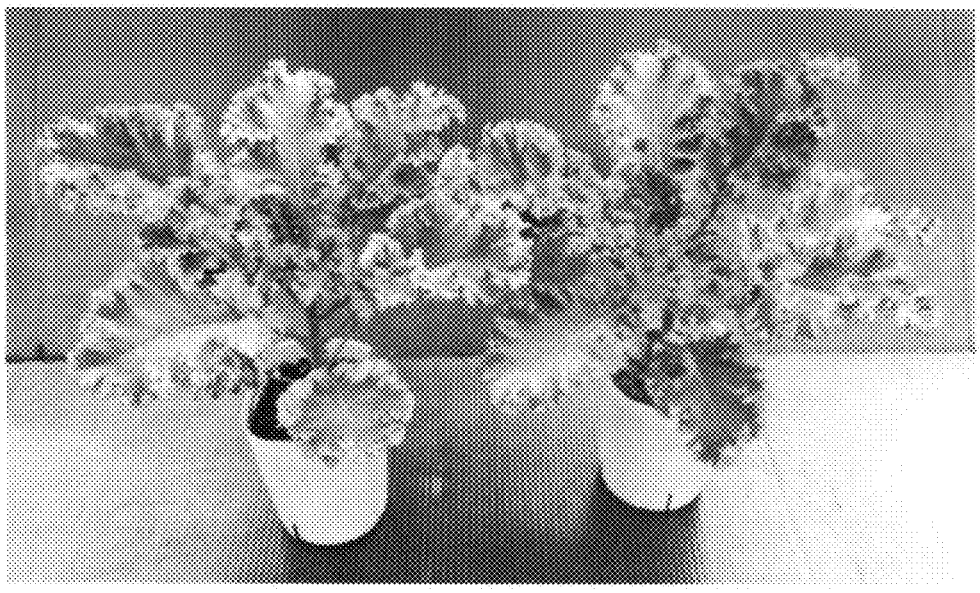
Figure 2:
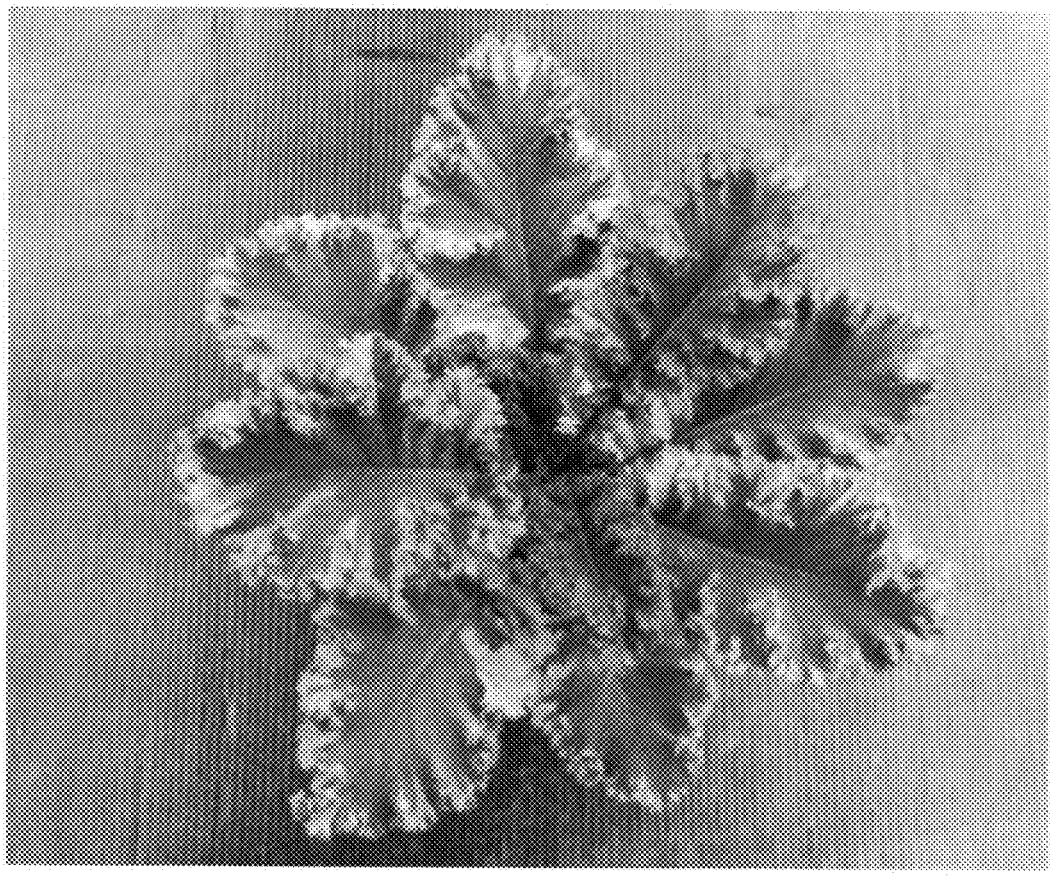

The photograph in FIG. 2 provides a top view of a plant of 'Purple Varie'.

The colors in the photograph may differ slightly from the color values cited in the detailed botanical description, which accurately describe the colors of the new *Brassica.*

DETAILED BOTANICAL DESCRIPTION OF THE PLANT

The following is a detailed description of plants 6-months in age as grown in 9-cm containers in a greenhouse in Tabei-cho, Isesaki-shi, Gunma, Japan (with a single pinch at 4 months). The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Flowers not observed.

*Plant type*.—Herbaceous perennial/biennial that is grown as an annual.

*Plant habit*.—Upright, ovate in overall plant shape.

*Height and spread*.—Reaches about 20 cm in height and about 23 cm in width in a 9-cm container.

*Hardiness*.—U.S.D.A. Zones 7 to 10, but grown as an annual for single season use.

*Diseases and pests*.—No susceptibility or resistance to diseases or pests has been observed.

*Propagation*.—Stem cuttings.

*Root development*.—Roots initiate in about 2 weeks from cuttings and fully develop in a 9-cm container is about 5 months.

*Growth rate*.—Moderate.

*Vigor*.—Moderate.

Stem description:

*Stem size*.—Average of 15 cm in length and 4 mm in width.

*Stem aspect*.—Rounded and angulate (6 angles).

*Stem strength*.—Strong.

*Stem color*.—Young stem; N77B to N77D with waxy coating a color between N187D and 202C, mature stems; a color between N77A and 187A (closer to N77A).

*Stem surface*.—Glabrous with waxy coating.

*Internode length*.—6 mm.

*Branching*.—Single basal stems.

Foliage description:

*Leaf shape*.—Obovate.

*Leaf division*.—Simple.

*Leaf base*.—Hastate.

*Leaf apex*.—Coarsely praemorse.

*Leaf venation*.—Pinnate, upper surface; a color between N77B and N78A, mid rib conspicuous, lower surface; a color between N187A and 200B.

*Leaf margins*.—Bidentate and strongly undulate.

*Leaf attachment*.—Petiolate.

*Leaf arrangement*.—Alternate.

*Leaf surface*.—Smooth and glabrous on upper and lower surface.

*Leaf substance*.—Thick and slightly rubbery.

*Leaf color*.—Emerging upper and lower surface; 137C with margins 175C, young upper surface; 137D with margins 160A and 73B, young lower surface; 138B with margins 160A and 73B, mature upper surface; 137A with margins primarily 73B with some areas of 160B and 157A, mature lower surface; N138B with margins primarily 73B with some areas of 160B and 157A.

*Leaf size*.—Average of 11 cm in length and 7.2 cm in width.

*Leaf quantity*.—Average of 10 leaves per stem.

*Leaf durability to stress*.—Moderate.

*Leaf aspect*.—Held at an average of 50° angle (90° vertical), mature to an arching aspect, slightly concave from midrib.

*Petioles*.—Average of 4 cm in length and 3 mm in width, color on upper surface a color between N77B and N78A with waxy layer N187D, color on lower surface N77B to N77 with waxy layer N187D, surface is glabrous, smooth and waxy, strength moderate.

Flower description: Flowers have not been observed as plants are grown as annual for its foliage and has only been grown under conditions (warm temperatures) to prevent flowering.

*Fruit and seed*.—None.

It is claimed:

1. A new and distinct cultivar of *Brassica* plant named 'Purple Varie' as herein illustrated and described.

* * * * *